United States Patent [19]
Watanabe et al.

[11] Patent Number: 5,328,835
[45] Date of Patent: Jul. 12, 1994

[54] EXPRESSION OF IMMUNOLOGICALLY REACTIVE HIV ENVELOPE PROTEINS

[75] Inventors: Suan M. Watanabe; Wesley L. Cosand; Susan McArdle; Bruce M. Travis, all of King, Wash.

[73] Assignee: Bristol-Myers Squibb Company, New York, N.Y.

[21] Appl. No.: 933,980

[22] Filed: Aug. 24, 1992

Related U.S. Application Data

[63] Continuation of Ser. No. 602,890, Oct. 24, 1990, abandoned, which is a continuation of Ser. No. 721,237, Apr. 8, 1985, abandoned.

[51] Int. Cl.$^5$ ............... C12N 15/49; C12N 15/63; C12N 15/71; C12P 21/02
[52] U.S. Cl. .................. 435/69.3; 435/5; 435/71.2; 435/172.1; 435/172.3; 435/252.3; 435/252.33; 435/320.1; 435/974; 536/23.1; 930/221; 935/12; 935/27; 935/40; 935/72; 935/73
[58] Field of Search .......... 435/69.3, 252.3, 252.33, 435/320.1, 5, 172.1, 172.3, 974; 536/23.1; 930/221

[56] References Cited

U.S. PATENT DOCUMENTS 4,520,113  5/1985  Gallo et al. ............... 435/5
4,774,175  9/1988  Chang et al. ............. 435/5

FOREIGN PATENT DOCUMENTS 0181150  5/1986  European Pat. Off. .
0185444  6/1986  European Pat. Off. .
0187041  7/1986  European Pat. Off. .
WO86/02383  4/1986  PCT Int'l Appl. .

OTHER PUBLICATIONS

Hopp et al., *Proc. Nat'l Acad. Sci. USA*, 78:3824-8 (1981).
Basak et al., *Virology* 128:77-91 (1983).
Kiyokawa et al., *Proc. Nat'l Acad. of Sci. USA*, vol. 81: 6202-6 (Abstract) (1984).
Crowl et al., *Cell*, 41: 979-988 (Jul., 1985).
Cabradilla et al., *Bio/Technology*, 4:128-132 (Feb., 1986).
F. Barre-Sinoussi et al., "Isolation of a T-Lymphotropic Retrovirus from a Patient at Risk for Acquired Immune Deficiency Syndrome (AIDS)", *Science* 220:868-871, 1983.
M. Popovic et al., "Detection, Isolation and Continuous Production of Cytopathic Retroviruses (HTLV-III) from Patients with AIDS and Pre-AIDS", *Science* 224:497-500, 1984.
J. A. Levy et al., "Isolation of Lymphocytopathic Retroviruses from San Francisco Patients with AIDS", *Science* 225:840-842, 1984.
S. Wain-Hobson et al., "Nucleotide Sequence of the AIDS Virus, LAV", *Cell* 40:9-17, 1985.
M. A. Muesing et al., "Nucleic Acid Structure and Expression of the Human AIDS/Lymphadenopathy Retrovirus", *Nature* 313:450-458, 1985.

(List continued on next page.)

Primary Examiner—Jacqueline Stone
Assistant Examiner—Johnny F. Railey, II
Attorney, Agent, or Firm—Townsend and Townsend

[57] ABSTRACT

A method for expressing proteins which are immunologically reactive with antibodies to lymphadenopathy-associated virus (LAV), now known as Human Immunodeficiency Virus (HIV), is disclosed. The proteins are produced by bacterial host cells transformed with a recombinant plasmid which includes appropriate procaryotic transcriptional and translational signals for expression, followed in·reading phase by a DNA sequence comprising a portion of the env region of the LAV genome. This portion codes for a protein which is immunologically reactive with antibodies to LAV, or antibodies to viruses defined to be the same as or equivalent to LAV. The proteins produced by the method disclosed may be used to screen for the presence of antibodies to LAV in a biological fluid, to determine the presence of LAV antigen in a biological fluid, or within a method for producing antibodies to LAV through the immunization of an animal with the protein.

17 Claims, 6 Drawing Sheets

OTHER PUBLICATIONS

R. Sanchez-Pescador et al., "Nucleotide Sequence and Expression of an AIDS-Associated Retrovirus (ARV-2)", Science 227:484-492, 1985.

J. Schupbach et al., "Serological Analysis of a Subgroup of Human T-Lymphotropic Retroviruses (HTLV-III) Associated with AIDS", Science 224:503, 1984.

J. Schupbach et al., "Antibodies to HTLV-III in Swiss Patients with AIDS and Pre-AIDS and in Groups at Risk for AIDS", New Engl. J. Med. 312:265-270, 1985.

Luc Montagnier et al., "Adaptation of Lymphadenopathy Associated Virus (LAV) to Replication in EBV--Transformed B Lymphoblastoid Cell Lines", Science 225:63-66, 1984.

J. B. Konopka et al., "Only Site-Directed Antibodies Reactive with the Highly Conserved src-Homologous Region of the v-abl Protein Neutralize Kinase Activity", J. Virol. 51:223-232, 1984.

Sarngadharan, M. G. et al., 1984, Antibodies Reactive with Human T-Lymphotropic Retroviruses (HTLV-III) in the Serum of Patients with AIDS. Science 224:506-509.

Kalyanaraman, V. S. et al., 1984, Antibodies to the Core Protein of Lymphadenopathy-Associated Virus (LAV) in Patients with AIDS. Science 225:321-323.

Laurence, J. et al., 1984, Lymphadenopathy-Associated Viral Antibody in AIDS: Immune Correlations and Definition of a Carrier State. New Engl. J. Med. 311:1269-1273.

Vilmer, E. et al., 1984, Isolation of New Lymphotropic Retrovirus from Two Siblings with Haemophilia B, One with AIDS. Lancet i:753-757.

Kitchen, L. W. et al., 1984, Aetiology of AIDS-Antibodies to Human T-cell Leukemia Virus (type III) in Haemophiliacs. Nature 312:367-369.

Chang, N. T. et al., 1985, Expression in E. coli of Open Reading Frame Gene Segments of HTLV-III. Science 228:93-96.

FIG. 1.

pJH11:  5' GAG ATC CCC GGG CGA GCT CGA ATT CGA GCT
⌐BamHI⌐
CGC CCG GGG ATC CTC TAG AGT CGA CCT GCA
⌐HindIII⌐
GCC CAA GCT T  3'

⌐BamHI⌐
pJH12:  5' GAG ATC CCC GGG GAT CCT CTA GAG TCG ACC
⌐HindIII⌐
TGC AGC CCA AGC TT  3'

⌐BamHI⌐
pJH14:  5' GAG ATC CCC CCG AAT TCG GGG GA TCC TCT
⌐HindIII⌐
AGA GTC GAC CTG CAG CCC AAG CTT  3'

EXPRESSION OF IMMUNOLOGICALLY REACTIVE HIV ENVELOPE PROTEINS

This is a continuation of application Ser. No. 07/602,890 filed Oct. 24, 1990, now abandoned which is a continuation of application of Ser. No. 06/721,237, filed Apr. 8, 1985, now abandoned.

TECHNICAL FIELD

The present invention relates generally to the expression of viral proteins through the use of recombinant DNA technology, and more specifically, to the expression of proteins which are immunologically reactive with antibodies to lymphadenopathy-associated virus (LAV), now known as Human Immunodeficiency Virus (HIV).

BACKGROUND ART

Acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, known as lymphadenopathy-associated virus (LAV) (Barré-Sinoussi et al., *Science* 220: 868 (1983)). Similar viruses have been reported by other scientific groups (Popovic et al., *Science* 224: 497 (1984); Levy et al., *Science* 225: 840 (1984)) and designated human T-cell lymphotropic virus type III (HTLV-III), AIDS-associated retrovirus (ARV), or immune deficiency-associated virus (IDAV). Still more recent data indicates that LAV, HTLV-III, ARV, and IDAV share several important characteristics, including substantial nucleotide homology (Wain-hobson et al., *Cell* 40: 9 (1985); Muesing et al., *Nature* 313: 450 (1985); Sanchez-Pescador et al., *Science* 227: 484 (1985)), and should be considered isolates of the same virus, although there is a likelihood that strain-to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, *supra;* Schupbach et al., *Science* 224:503 (1984)).

As noted above, the virus is known to be transmissable through blood products (blood, blood serum, blood plasma, and fractions thereof), making it important to screen the blood products to determine if the donor has been exposed to the virus. This can be done in any of several ways, including enzyme-linked immunosorbent assay (ELISA) for the detection of antibodies to LAV and related viruses. Individuals whose blood contains antibodies to LAV are said to be "seropositive." Blood from seropositive donors may be eliminated from the blood supply upon detection, thereby helping to prevent the spread of the disease.

The immune response of individuals exposed to LAV is variable. Antibodies can be produced to any of several viral proteins, including p13, p18, p25, p36, gp43, p55, gp110, etc. (Schupbach et al., *New Engl. J. Med.* 312: 265 (1985)). Not all individuals will make antibodies to the same proteins or to the same epitope on a given protein.

The detection of seropositive individuals, as currently practiced, has several inherent problems. Foremost among these problems is the need to isolate antigen from whole viruses for the immunological assays. This isolation requires the manipulation of large volumes of live, potentially infectious virus, and as such poses a significant safety hazard. In addition, there are concerns relating to the yield, purity, and reproducibility of virus from one preparation to another. This may result in an unacceptable number of false positives and/or negatives. Consequently, there is a need in the art for alternative methods of producing viral antigens which are useful in blood screening assays and which further provide other related advantages.

DISCLOSURE OF INVENTION

Briefly stated, the present invention discloses DNA sequences comprising a portion of the envelope (env) region of the LAV genome, the portion coding for a protein which is immunologically reactive with antibodies to LAV. A recombinant plasmid capable of replication in bacterial host cells is also disclosed. The plasmid includes procaryotic transcriptional and translational signals for expression, followed in reading phase by the DNA sequence described above. In a preferred embodiment, signals are chosen from an operon, such as the trp operon, which is inducible and/or suppressible. Bacterial cells, such as *E. coli*, which have been transformed with the recombinant plasmid described above, are also disclosed.

Another aspect of the invention discloses a method for preparing proteins which are immunologically reactive with antibodies to LAV. The method comprises introducing into a bacterial host cell a recombinant plasmid capable of replication in bacterial host cells. The plasmid includes procaryotic transcriptional and translational signals for expression, followed in reading phase by a DNA sequence comprising a portion of the env region of the LAV genome, the portion coding for a protein which is immunologically reactive with antibodies to LAV. Subsequent to the introduction of the plasmid, the bacterial host is grown in an appropriate medium. Expression of the protein is then induced and the protein product of the Sequence is isolated from the bacterial host. The protein product may be purified subsequent to isolation, as by gel permeation chromatography.

A further aspect of the invention discloses a method for determining the presence of antibodies to LAV in a biological fluid. The method comprises incubating the biological fluid with a protein produced by bacterial cells transformed with a recombinant plasmid as described above, thereby forming a reaction mixture, and subsequently analyzing the reaction mixture to determine the presence of the antibodies. In a preferred embodiment, the step of analyzing the reaction mixture comprises contacting the reaction mixture with a labeled specific binding partner for the antibody.

Yet another aspect of the invention discloses a method for determining the presence of LAV antigen in a biological fluid, comprising incubating the biological fluid with a labeled protein produced by bacterial cells transformed with a recombinant plasmid as described above, and either sequentially or simultaneously, with an antibody to the protein such that specific binding occurs. Subsequently, the reaction mixture formed during the incubation is analyzed to determine the amount of label associated with the antibody.

A method for producing antibodies to LAV comprising immunizing an animal with a protein produced by bacterial cells transformed with a recombinant plasmid as described above, is also disclosed.

Other aspects of the invention will become evident upon reference to the following detailed description and attached drawings.

BEST MODE FOR CARRYING OUT THE INVENTION

Prior to setting forth the invention, it may be helpful to an understanding thereof to set forth definitions of certain terms to be used hereinfter.

Lymphadenopathy-Associated Virus (LAV): A human T-lymphotropic retrovirus. For purposes of the present invention, a virus is considered to be the same as or equivalent to LAV if it substantially fulfills the following criteria:

(a) the virus is tropic for T-lymphocytes, especially T-helper cells (CD4+, according to the international nomenclature defined in Bernard et al., eds., *Leucocyte Typing*, New York: Springer Verlag (1984));

(b) the virus is cytopathic for infected CD4+ cells (rather than transforming, as are HTLV-I and II);

(c) the virus encodes an RNA-dependent DNA polymerase (reverse transcriptase) which is $Mg^{2+}$-dependent (optimum concentration 5 mM, optimum pH 7.8, not inhibitable by actinomycin D) and can employ oligo $(dT)_{12-18}$ as a primer for reverse transcription from its 3' LTR;

(d) the virus bands in a sucrose gradient at a density of approximately 1.16;

(e) the virus can be labeled with [$^3$H] uridine;

(f) the virus is distinct by immunological and nucleotide sequence criteria from members of the HTLV-I/II family of viruses (by this criterion HTLV-III is not to be considered a member of the HTLV-I/II family);

(g) the virus is substantially cross-reactive immunologically with the proteins encoded by the gag and env regions of LAV; and (h) the virus shares substantial nucleotide homology (78-100%) and amino acid sequence homology (90-100%) with LAV.

Immunologically Reactive: An antigen and an antibody are said to be "immunologically reactive" if they are capable of binding specifically to each other, typically with an affinity of at least $10^6 M^{-1}$, more often at least $10^8 M^{-1}$.

Transformed or Transformation: The process of stably and heritably altering the genotype of a recipient cell or microorganism by the introduction of purified DNA.

Lymphadenopathy-associated virus (LAV) can be isolated from patients with AIDS or lymphadenopathy syndrome. The lymph nodes of such patients are typically biopsied and placed in culture medium supplemented as necessary to support growth. A mitogen such as interleukin-2 (IL-2) or phytohemagglutinin (PHA) can be included; antiserum to human interferon can also be included. Reverse transcriptase activity typically appears about day 15 of culture, indicating the presence of virus. The virus can be concentrated from the culture supernatant using a nonionic detergent, followed by banding in a sucrose gradient. These and other methods of purification are well known in the art and are described, for example, in Montelaro et al., *J. Virology* 42: 1029 (1982).

LAV can be propagated in any of a number of ways. It can be cultured in T-lymphocytes derived from umbilical cord or peripheral blood or bone marrow. Alternatively, it can be propagated in immortalized T-cells or B-cells; see, for example, Popovic et al., *Science* 224: 497 (1984), and Montagnier et al., *Science* 225: 63 (1984). Growth of the virus is usually monitored by the presence of reverse transcriptase activity.

A genomic clone of LAV can be prepared by any of several methods well known in the art, including but not limited to those described by Hahn et al., *Nature* 312:166 (1984); Alizon et al., *Nature* 312: 757 (1984); Luciw et al., *Nature* 313: 760 (1984); and Muesing et al., *Nature* 313: 450 (1985).

Briefly, in one of these methods (Alizon et al.) DNA is isolated from LAV-infected T-cells of a healthy donor, partially digested with a restriction endonuclease such as Hind III, and the resultant digest fractionated electrophoretically. Fragments which correspond in size to the size of the entire LAV genome (approximately 9.2 Kb) are eluted from the gel, precipitated, resuspended, and ligated into the arms of an appropriately restricted vector. The ligation mix is packaged into bacteriophage particles. Bacteria are transformed with the bacteriophage, and the clones are screened in situ for LAV inserts using a suitable probe (such as a cDNA made from LAV-RNA). From such a clone, the desired region of LAV can be subcloned into a bacterial plasmid vector, such as pUC 18. Further subcloning can be desirable to remove unwanted sequences and to add additional restriction sites (in the form of a polylinker) at either end for the purpose of facilitating cloning into an expression vector.

The LAV sequences can then be subcloned into an inducible expression vector. A variety of expression vectors are known in the art and include λgt 11:Tn5 (Hall et al., *Nature* 311: 379 (1984); trp E (Paul et al., *Euro. J. Cell Biol.* 31:171 (1983); pINIII (Masui et al., *Biotechnology*, January 1984, p. 81).

The resultant proteins can be partially purified and used for a variety of purposes, including, as immunogens and antigens in immunoassays. For use as immunogens, the proteins can be injected into an animal, such as a mouse, rabbit, goat, etc., either in buffered solution or in adjuvant. Alternatively, the proteins can be purified by polyacrylamide gel electrophoresis and the bands of interest cut out from the gel, triturated, and resuspended in buffer for injection into the host animal. Polyclonal or monoclonal antibodies can be prepared. For use as antigens in immunoassays, the proteins can be employed in labeled or unlabeled form. Where they are labeled, the labels can include radioisotopes, fluorophores, enzymes, luminescers, or particles. These and other labels are well known in the art and are described, for example, in the following U.S. Pat. Nos.: 3,766,162; 3,791,932; 3,817,837; 3,996,345; and 4,233,402.

Assays employing the recombinant proteins of the instant invention can be heterogeneous (i.e., requiring a separation step) or homogeneous. If the assay is heterogeneous, a variety of separation means can be employed, including centrifugation, filtration, chromatography, or magnetism.

One preferred assay for the screening of blood products or other physiological fluids for the presence of antibodies is an ELISA assay. Typically, antigen (in this case, one or a combination of recombinant proteins) is adsorbed to the surface of a microtiter well. Residual protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1–5.0% by weight) of protein, such as BSA, NGS, or BLOTTO. After incubating for a sufficient length of time to allow specific binding to occur, the well is washed to remove unbound protein and then incubated with a labeled, anti-human immunoglobulin antibody (a HuIg). The label can be chosen from a variety of enzymes, including horseradish peroxidase (HRP), $\beta$-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

For convenience, reagents for ELISA assays may be provided in the form of kits. These kits can include microtiter plates to which vital proteins made by recombinant techniques have been pre-adsorbed, various diluents and buffers, labeled conjugates for the detection of specifically bound antibodies, and other signal-generating reagents, such as enzyme substrates, cofactors, and chromogens.

Due to the fact that a significant number of AIDS patients are highly immunosuppressed and have progressively lost the ability to make high-titer antibodies, the present invention utilizes portions of the envelope (env) region of the LAV genome which codes for a protein which is immunologically reactive with antibodies to LAV. The presence of antibodies to the envelope glycoprotein of LAV is a better indicator of LAV infection than is the presence of antibodies to other vital proteins, because the antibody titers to the envelope glycoprotein are thought to persist during the later stages of the disease, while antibody to other proteins, such as the core protein, may decline to less than detectable levels.

In the following example, an LAV genomic clone designated λJ19 was subcloned into the bacterial plasmid vector, pUC 18. The resultant subclone, designated pBT-1, was further subcloned to yield pRS-3, which contained predominantly env, F, and LTR region sequences. The env and part of the F sequences were further subcloned into M13mp18, and then regions of the env sequence were transferred into the trp E inducible expression vector. The env DNA was inserted in-frame downstream of the trp E gene, resulting in the expression of a trp E-env fusion protein when $E.$ $coli$ were transformed with this construct. The resultant proteins were partially purified and characterized by their reactivity in ELISA with sera from known seropositive and known seronegative individuals. Five useful constructions, designated pENV-1 to pENV-5, were identified.

The following example is offered by way of illustration, and not by way of limitation.

EXAMPLE

A. CONSTRUCTION OF THE trp-env EXPRESSION VECTORS

Any of several bacterial expression systems can be used to express foreign proteins. The trp E system was chosen for the expression of LAV env sequences because it contains a strong inducible promoter, but its expression can also be suppressed so that foreign (and potentially toxic) protein does not accumulate within the bacteria for long periods of time.

Since there is no rapid and convenient way to screen or select for bacteria transformed with vector containing a foreign insert (as opposed to bacteria transformed with vector alone), it is convenient to subclone the desired region of a large piece of DNA (such as λphage DNA) into a vector containing a selection system for inserts before transferring it to the trp E expression vector. This facilitates the screening of transformed bacteria for ones containing the desired insert.

Figure 1:
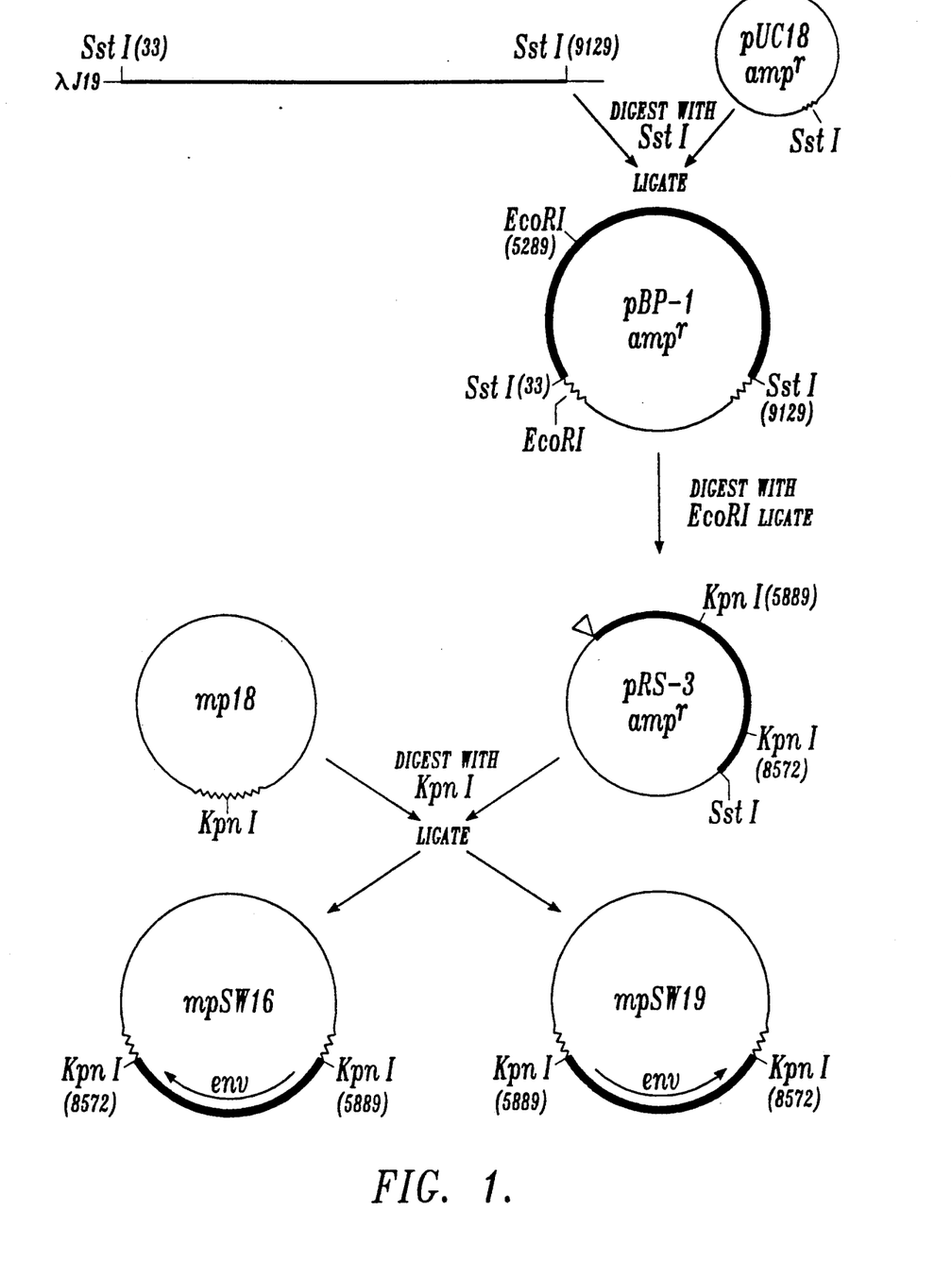
FIG. 1 illustrates the construction of mpSW16 and mpSW19 from λJ19.

Our strategy, therefore, was to first subclone i n two steps most of the env region of the LAV genome into a transfer vector, M13mp18 (FIG. 1). Then, various fragments of this subclone were ligated into either of three trp expression vectors (pJH 11, pJH 12, pJH 14) which differed only in the reading frame of the restriction sites in the polylinker region (see FIG. 2). Some of the resulting subclones (e.g., pENV-5, pENV-4) were used as such, but others required further modifications (pENV-1, pENV-2, pENV-3) to produce the desired product.

1. SUBCLONING LAV GENOME a. Preparation of phage DNA

The entire LAV genome was obtained from the Pasteur Institut in the form of λ phage particles containing a 9.2 Kb genomic DNA insert in the Hind III site of phage λ L47.1. This clone is referred to as λ J19 and is described in Wain-Hobson et al., Cell 40: 9 (1985). λ J19 phage particles were transfected into the Q359 strain of $E.$ $coli$ K-12 (the genotype of Q359 is hsdRk−, hsdMk+, supF $\phi$80, P2) according to the procedure of Maniatis et al., Molecular Cloning: A Laboratory Manual, New York: Cold Spring Harbor Laboratory, 1982, at p. 64. A single plaque was picked and the phage amplified by the plate lysate method (Maniatis, supra, at p. 65). After a nine-hour incubation at 37° C., the plates (100 mm diameter) containing confluent plaques were overlaid with 5 ml of 100 mM NaCl/20 mM MGSO$_4$/50 mM Tris, pH 7.5. After incubating for twelve hours at 4° C., the liquid was collected and extracted two times with an equal volume of chloroform.

To 10 ml of the resultant aqueous phase containing phage particles was added 2 ml 0.25M EDTA/2.5% SDS/0.5M Tris, pH 9, and the suspension was incubated at 70° C. for fifteen minutes to disrupt the phage.

2.5 ml 8M potassium acetate was added, and the solution was incubated on ice for fifteen minutes, then centrifuged for ten minutes at 12,000 xg at 4° C. to pellet protein. The supernatant was transferred to a 50 ml polypropylene centrifuge tube and extracted with an equal volume of phenol (pH 8, equilibrated with 1M Tris, pH 8) at 20° C. The aqueous phase was then extracted with an equal volume of chloroform:isoamylalcohol (24:1), at 20° C. To the aqueous phase was then added 2.5 volumes of 95% ethanol to precipitate the DNA. After centrifugation, the DNA pellet was dried and resuspended in 10 mM Tris HCl, pH 7.4/1 mM EDTA.

b. Subcloning the env region

Approximately 12 ug of λ J19 DNA prepared in A.1.a above was digested to completion with the restriction enzyme Sst I (Bethesda Research Labs, Bethesda, Md.), which only cuts in the LTR regions of this isolate of LAV. The digest mixture was electrophoresed at 1 V/cm through 0.9% agarose in 0.089M Tris-borate/0.089M boric acid/1 mM EDTA. The position of the 9.1 Kb fragment was determined relative to molecular weight standards after staining with ethidium bromide. This band was electroeluted into NA45 paper (Schleicher and Schuell, Keene, N.H.). The DNA was recovered from the paper according to instructions provided by the manufacturer.

The 9.1 Kb Sst I fragment was ligated into the Sst I digested vector pUC 18, at a ratio of 10 insert molecules: 1 vector molecule. *E. coli* strain HB101 was transformed with the ligation mix by the $CaCl_2$ procedure of Maniatis, et al. (supra) and plated onto LB plus ampicillin (200 ug/ml) agar plates.

Single colonies were picked and diluted into 3 ml LB plus ampicillin medium and grown overnight at 37° C. with constant shaking. Plasmid DNA was prepared by the alkaline lysis method (Maniatis et al., supra, at p. 368). One colony was selected which contained the 9.1 Kb Sst I insert in an orientation such that the Eco RI site in the polylinker was closest to the 5' end of the LAV genome, as determined by restriction analysis of the plasmid DNA. This subclone was designated pBT-1 (ATCC Accession #53069) (FIG. 1).

Plasmid pBT-1 was then digested with Eco RI, and the vector, still containing the 3' end of the LAV genome, was religated. This served to remove the 5' Eco RI fragments from the plasmid. HB101 cells were transformed with the ligation mixture, and a colony containing the insert pRS-3 was identified by restriction analysis of the purified plasmid DNA.

The sequence between the Kpn I sites at bp 5889 and bp 8572 [numbering according to Wain-Hobson et al., *Cell* 40: 9 (1985)], containing most of the env region, was then transferred from pRS-3 to the M13mp18 vector. This was done to further remove extraneous (non-env) sequences and also to place the env sequences in a vector which utilizes β-galactosidase rather than ampicillin as the selectable/screenable marker. This was advantageous because the trp E expression vector uses ampicillin resistance as its selectable marker; transfer of an insert from one vector (pUC 18) encoding the ampicillin resistance factor to another (trp expression vectors pJH 11,12,14) would make screening for the desired insert plus vector more difficult. M13 phage were screened by using the chromogenic substrate 5-bromo-4-chloro-3-indolyl-β-galactoside (Sigma Chemical Co.) to score for inactivation of β-galactosidase due to insertion of env sequence. Those phage containing inserts were screened for the orientation of the insert relative to restriction sites in the polylinker region. DNA was isolated from recombinants (mpSW16, mpSW19) for each orientation (FIG. 1).

2. INSERTION OF THE ENV SEQUENCE INTO TRP VECTORS

Figure 2:
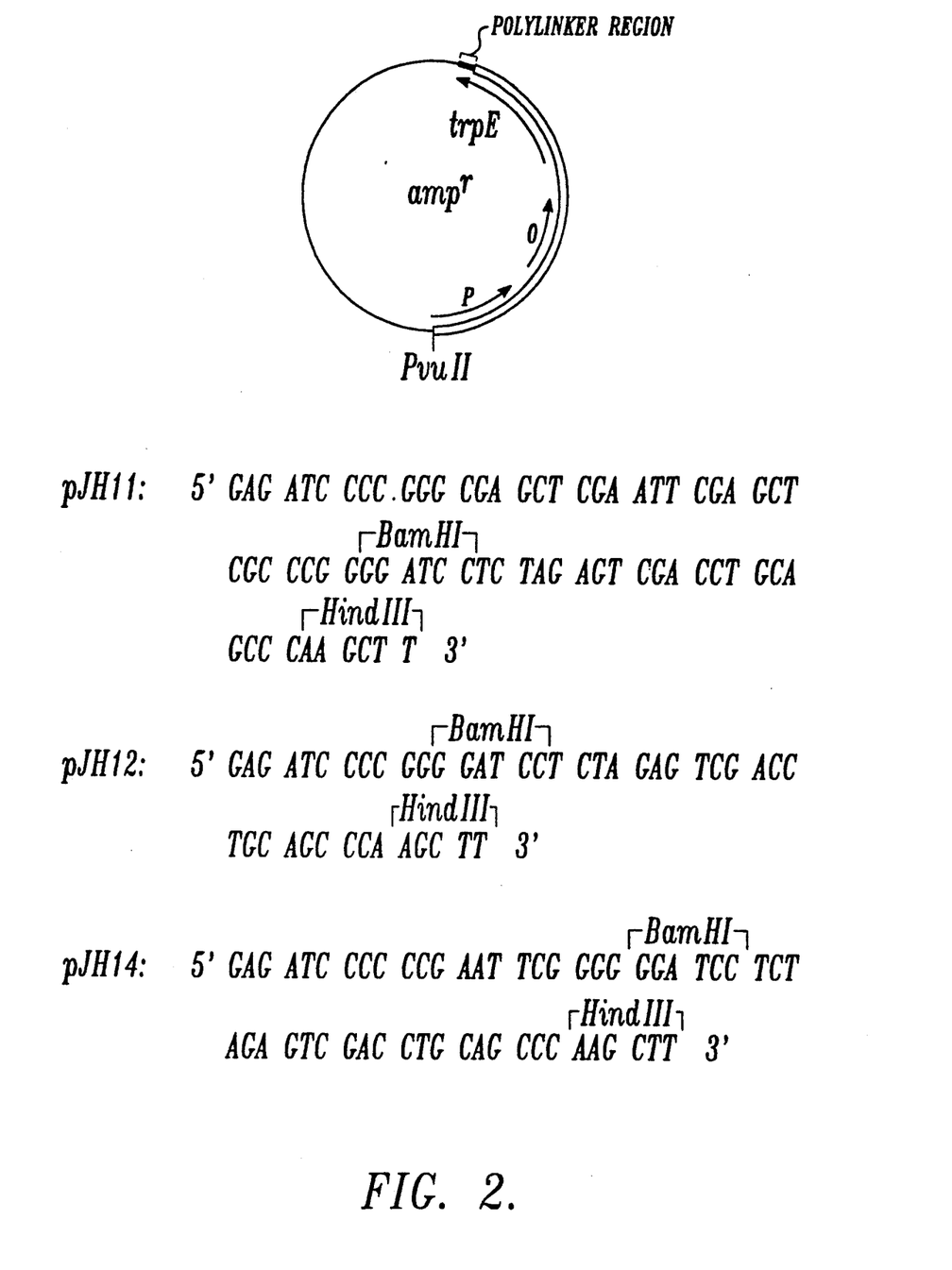
FIG. 2 illustrates the trp E expression vectors pJH 11, pJH 12, and pJH 14, including the polylinker sequences.

The expression vectors contained the *E. coli* trp operon promoter, operator, and trp E gene inserted into pBR322 (FIG. 2). The trp E gene was truncated at its 5'-most Bgl II site by the insertion of a polylinker sequence (Konopka et al., *J. Virol* 51: 223 (1984)). The different trp vectors (pJH 11, pJH 12, and pJH 14) differed according to the reading frame of the restriction sites within the polylinker region. Insertion of an open reading frame into the appropriate vector results in the production of a fusion protein with trp E sequences at the amino terminal end (Spindler et al., *J. Virol* 49:132 (1984)).

Figure 3:
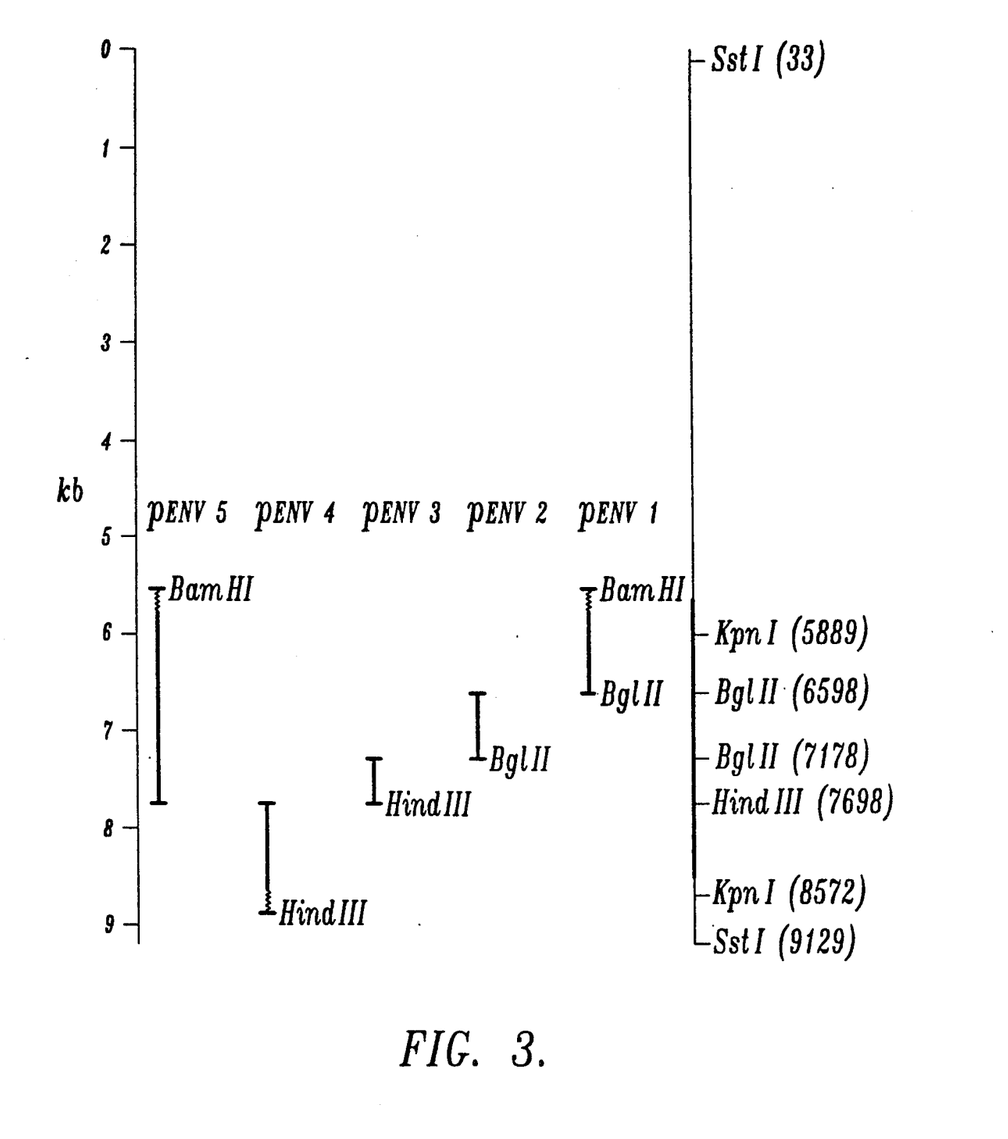
FIG. 3 illustrates the origin of the LAV inserts in pENV-1, pENV-2, pENV-3, pENV-4, and pENV-5.
Figure 4:
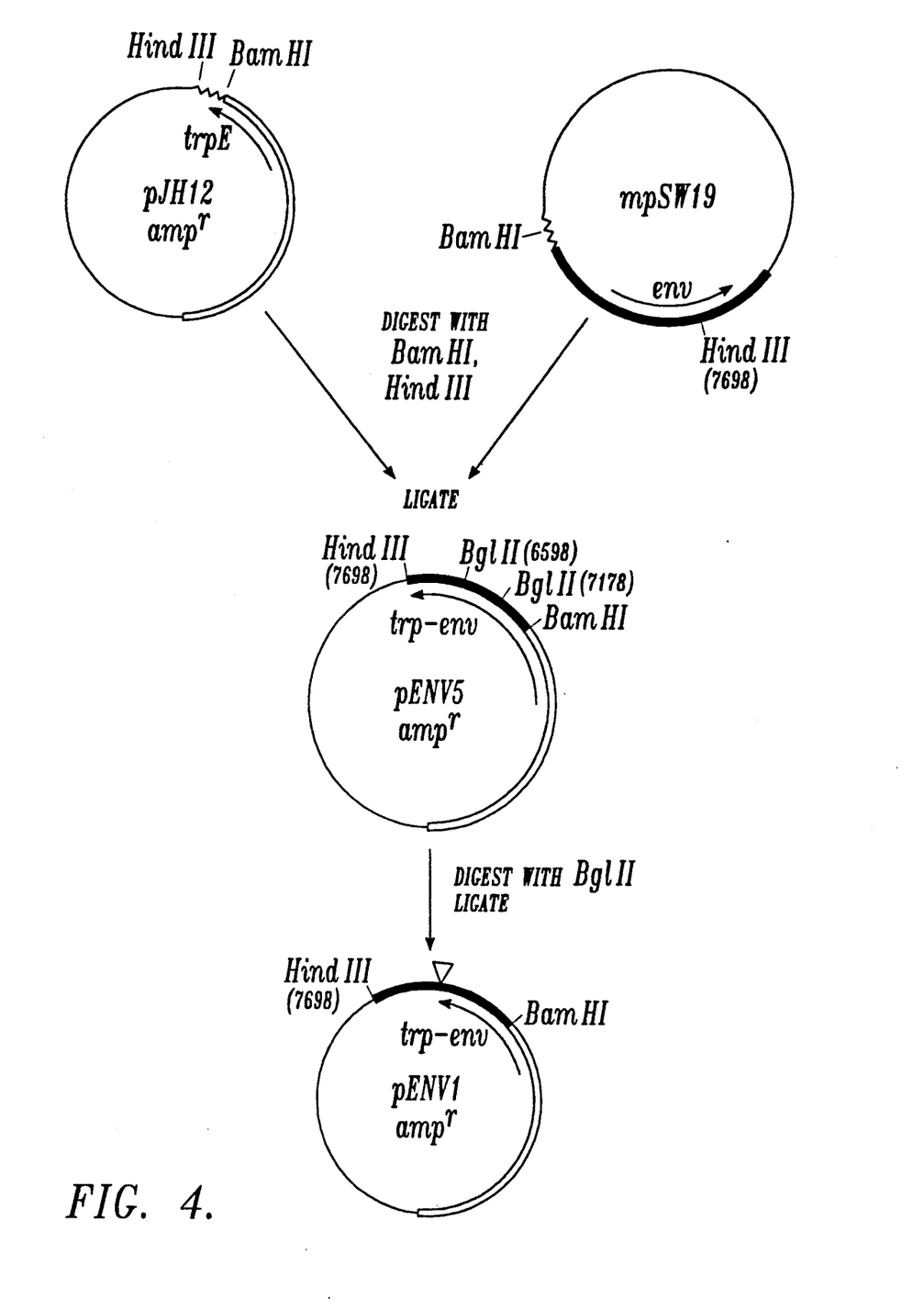
FIG. 4 illustrates the construction of pENV-5 and pENV-1 from pJH 12 and mpSW19.
Figure 5:
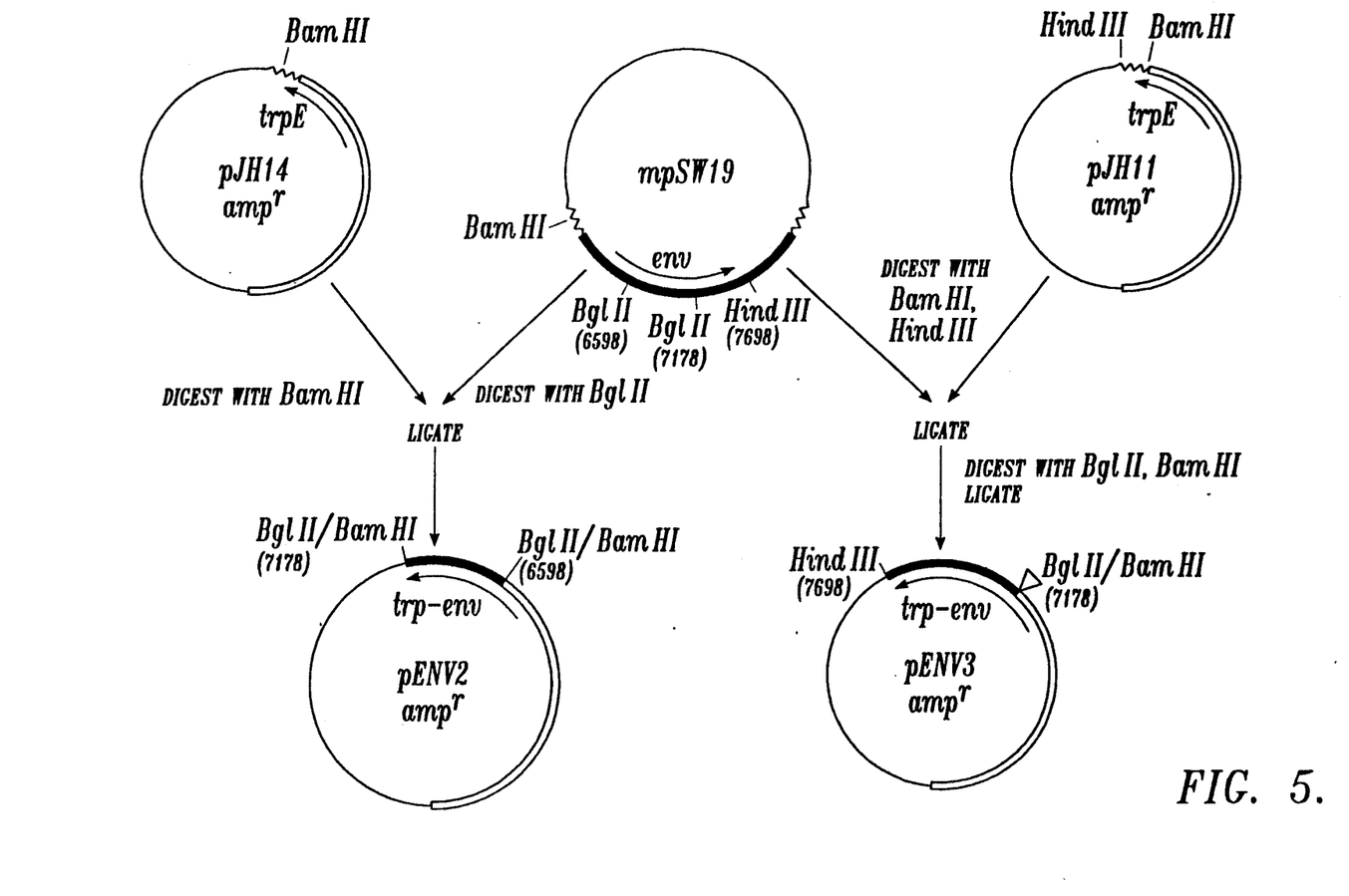
FIG. 5 illustrates the construction of pENV-2 from pJH 14 and mpSW19, and the construction of pENV-3 from pJH 11 and mpSW19.
Figure 6:
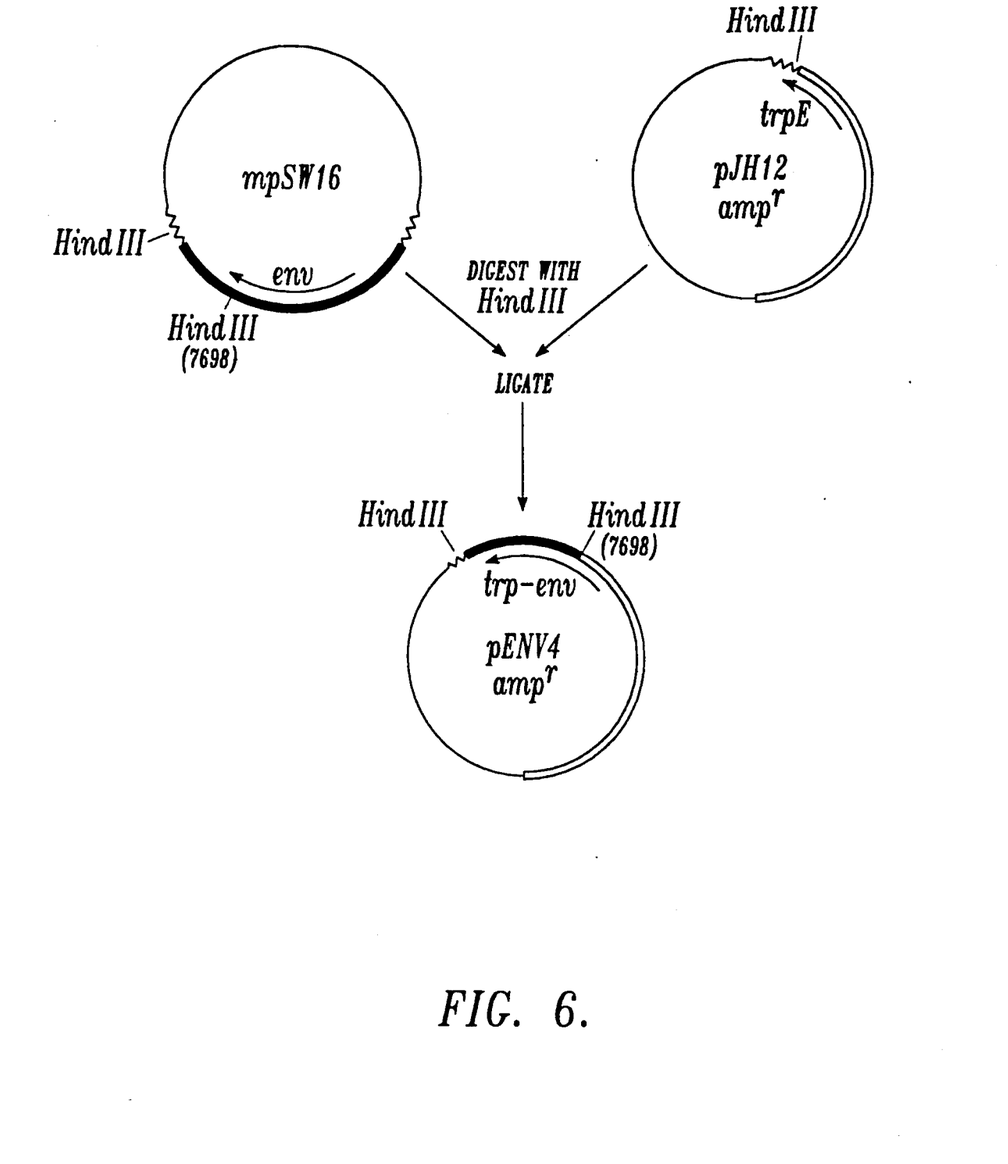
FIG. 6 illustrates the construction of pENV-4 from pJH 12 and mpSW16.

We selected five overlapping regions of LAV-env for expression (FIG. 3). Our choice was dictated by the limitation on insert size in these vectors (Konopka et al., *J. Virol* 51: 223 (1984)) and by the location of hydrophobic sequences, which may be deleterious for expression.

pENV-5 (ATCC Accession #53074) was constructed by ligating the env region from mpSW19's Bam H1 site in the polylinker region to the env Hind III site (bp #7698) into Bam H1 and Hind III (New England Biolabs) restricted pJH 12 (FIG. 4). Ligations were transformed into $CaCl_2$-shocked E. coli HB101 and the bacteria plated in the presence of ampicillin (Sigma) at 100 ug/ml and tryptophan (Sigma) at 20 ug/ml. The tryptophan was added to suppress expression of the foreign protein, accumulation of which could be deleterious to the bacteria. Ampicillin-resistant colonies were screened by minilysates for the presence of recombinant plasmids containing the env fragment.

pENV-1 (ATCC Accession #53070) was derived from pENV-5 by deleting the sequences between the two Bgl II sites (bp 6598 and bp 7178) (FIG. 4). This deletion decreased the size of the open reading frame by introducing a stop codon shortly after the Bgl II site.

pENV-2 (ATCC Accession #53071) was constructed by inserting the fragment between two Bgl II sites (bp 6598 and bp 7178) into Bam H1 restricted pJH 14 (FIG. 5) (Bgl II and Bam H1 overhangs are compatible). E. coli HB 101 were transformed with the ligation reactions and the ampicillin-resistant colonies screened by restriction analysis for the presence and orientation of the env insert into pJH 14.

pENV-3 (ATCC Accession #53072) required ligation of the env region between mpSW19's Bam H1 site (in the polylinker) and Hind III site (bp 7698) into Bam H1 and Hind III restricted pJH 11 (FIG. 5). E. coli HB101 were transformed with the ligation reaction, and the ampicillin-resistant colonies were screened by minilysates. DNA from an appropriate colony was isolated, digested with Bam H1 and Bgl II (New England Biolabs), and religated. This DNA was used to transform *E. coli* HB101. The resultant ampicillin-resistant bacteria were screened by restriction analysis for recombinant plasmids which had deleted the Bam H1 to Bgl II fragment (FIG. 5). Deletion of the fragment brought the env sequences between the Bgl II site (bp 7178) and the Hind III site (bp 7698) into the correct reading frame.

pENV-4 (ATCC Accession #53073) was constructed by ligating the Hind III fragment from mpSW16 into pJH 12 which had been treated with Hind III and calf intestinal alkaline phosphatase (Boehringer Mannheim) (FIG. 6). Recombinant plasmids were identified by transforming *E. coli* HB101 with the ligation mixture and then screening by restriction analysis of minilysates.

*Escherichia coli* transformants containing pBT-1, pENV-1, pENV-2, pENV-3, pENV-4 and pENV-5 have been deposited as ATCC Deposit Nos. 53069, 53870, 53071, 53072, 53073 and 53074, respectively, at The American Type Culture Collection, 12301 Parklawn Drive, Rockville, Md. 20852 on Mar. 28, 1985.

B. PROTEIN EXPRESSION

1. TRANSFORMATION OF E. COLI WITH THE TRP-ENV CONSTRUCTS

Each of the recombinant trp-env expression plasmids was transferred from *E. coli* HB101 into *E. coli* C600 because the latter is a potentially better host for protein production. Transfer involved transformation of CaCl$_2$-shocked C600 with supercoiled DNA from minilysates of HB101. Bacteria were plated in the presence of ampicillin and tryptophan as described (Konopka et al., *J. Virol.* 51: 223 (1984)). Drug-resistant colonies were screened by minilysates to confirm the presence of the appropriate plasmid.

2. EXPRESSION OF TRP-ENV PROTEINS

Growth and induction of *E. coli* C600 transformed by the trp expression vectors were as described (Spindler et al., *J. Virol* 49:132 (1984); Konopka et al., *J. Virol.* 5.1:223 (1984)). Briefly, minimal medium containing tryptophan (20 ug/ml) and ampicillin (100 ug/ml) was inoculated with transformed bacteria from glycerol stocks. Cultures were grown with aeration at 37° C. overnight. The overnight cultures were then inoculated at 1:100 into fresh minimal medium containing ampicillin (100 ug/ml) but no tryptophan. These cultures were grown with aeration for 2-3 hours (up to early log phase) at 37° C . The inducer, 3-$\beta$-indoleacrylic acid (Sigma), was added to a final concentration of 20 ug/ml from freshly made stocks at 20 mg/ml in 95% ethanol.

Induced cultures were grown at 37° C. with aeration for 4 to 5 hours and then pelleted and, optionally, frozen. Protein yields from pENV-1, pENV-2, and pENV-3 were typically between 10-30 mg/liter, while the yields from pENV-4 and pENV-5 were typically less than 1 mg/liter.

C. ISOLATION AND PURIFICATION OF TRP-ENV PROTEINS

Fusion proteins were partially purified from cell pellets as described (Konopka et al., *J. Virol.* 51: 223 (1984)). Briefly, bacteria were resuspended in 100 ml of 50 mM Tris, pH 7.5/0.5 mM EDTA/150 mM NaCl (TNE) per liter of induced culture. Lysozyme (Sigma) was added to a final concentration of 1 mg/ml. After fifteen minutes at 0° C., NP40 was added to the mixture to a final concentration of 0.2% for ten minutes at 0° C. 1-2 mg of DNase (Sigma) was then added with 150 ml of DNase buffer (150 mM NaCl/12 mM MgCl$_2$). Reaction mixtures were incubated for one hour at 0° C. with frequent stirring. Insoluble proteins were then pelleted by centrifugation for fifteen minutes at 8000 xg at 0° C. Pellets were washed two times in TNE and then analyzed for the presence of insoluble proteins by denaturing polyacrylamide gel electrophoresis. Proteins were visualized by staining with Coomassie brilliant blue.

The pellet containing the insoluble material from one liter of bacteria was solubilized in 6 mls of 6M guanidinium chloride/0.1M Tris HCl, pH 7.8. To this solution was added approximately 60 mg of solid dithiothreitol (DTT), and the reduction was allowed to proceed for thirty minutes at 37° C.

The solubilized reduced protein was subjected to gel-permeation chromatography on a 9.4 mm×25 cm GF-250 Zorbax column (Du Pont, Wilmington, Del.). A 100 ul aliquot of the protein solution was injected onto the column and eluted with 6M guanidinium chloride at a flow rate of 0.5 ml/minute. The optical density at 280 nm was monitored, and fractions were collected at 30-second intervals. Fraction number 32, i.e., the fraction eluting between 7.75 and 8.00 mls, was used for the subsequent assays. Note: Inclusion of DTT will result in formation of insoluble metal sulfides when inferior grades of guanidinium chloride are used.

The trp-env fusion proteins have also been purified as follows:

Fusion proteins were partially purified from cell pellets as an insoluble pellet (described above). The pellet containing the insoluble material from four liters of bacteria was solubilized in 4 mls of 6M guanidinium chloride/0.1M Tris HCl, pH 7.8. To this solution was added approximately 100 mg of solid dithiothreitol (DTT), and the reduction was allowed to proceed for one hour at 37° C.

The solubilized, reduced protein was subjected to gel-permeation chromatography on a 2.6×87 cm column of Fractogel TSK HW-50(S) (MCB Manufacturing Chemists, Gibbstown, N.J.). The 4 mls of reduced protein were pumped onto the column and eluted with $2\times10^{-4}$M DTT/$2\times10^{-3}$ ethylenediaminetetraacetic acid (EDTA)/6M guanidinium chloride (American Research Products Co., South Euclid, Ohio). The column was run at 0.5 mls/minute, the optical density at 280 nm was monitored, and fractions were collected at ten-minute intervals. Fractions 34 and 35, the two fractions from the center of the UV absorbing peak, were used in subsequent assays.

D. IMMUNOLOGICAL REACTIVITY OF TRP-ENV PROTEINS

1. ANALYSIS BY WESTERN BLOTS

Aliquots from the insoluble protein preparations expressed by pENV-1, pENV-2, pENV-3, pENV-4, and pENV-5 were solubilized in 2% sodium dodecylsulphate/100 mM Tris, pH 6.8/20% glycerol/1.5M $\beta$-mercaptoethanol and electrophoresed on denaturing polyacrylamide gels. Proteins were electrotransferred onto nitrocellulose (BA85, Schleicher and Schuell, Keene, N.H.) and the filters blocked with 5% bovine serum albumin (Sigma). Filters were then probed with *E. coli*-adsorbed human sera pooled from AIDS patients. The filters were developed with HRP-conjugated goat $\alpha$ HuIg. The pool was reactive with all five trp-env fusion proteins but not with trp E protein alone.

2. ANALYSIS BY ELISA

Insoluble protein preparations of pENV-1, pENV-2, pENV-3, pENV-5, and trp E were solubilized in 3M guanidinium chloride. Insoluble material was removed by centrifugation at 15,000 xg for five minutes. Solubilized protein concentrations were determined by the method of Bradford (*Analytical Biochemistry* 72: 248 (1976)). The proteins were diluted in 0.05M carbonate/- bicarbonate buffer (pH 9.6) to a final concentration of 1–2 ug/ml. Fifty ul aliquots were loaded per microtiter well and incubated at 4° C. overnight. Plates were then blocked with BLOTTO (5% [w/v] nonfat dry milk/0.01% thimerosol/0.01% antifoam A in 0.01M sodium phosphate, pH 7.2/0.15M sodium chloride) for one hour at 37° C. Pooled seropositive sera, sera from male homosexuals or LAS patients, and sera from healthy heterosexuals were diluted 1:100 with a 1:1 mixture of BLOTTO and PBS (0.01M sodium phosphate, pH 7.3/0.15M NaCl), and 50 ul of diluted serum was added per well for one hour at 37° C. The sera were removed, and the plates were washed three times in wash buffer (0.15M NACl/0.05% [w/v] Tween 20) before adding 100 ul of the goat anti-human IgG/-horseradish peroxidase conjugate (diluted 1:10,000 in 50 mM NaCitrate/0.05% Tween 20/1% heat-inactivated normal goat serum; obtained from Antibodies, Inc., Davis, Calif.) for one hour at 37° C. The conjugate was removed and the plates washed three times with 0.15M NACl/0.05% (w/v) Tween 20. The ELISA assay was developed by adding 100 ul/well of substrate solution (10 mg o-phenylenediamine in 50 ml 0.05 M sodium citrate, pH 7.0) for thirty minutes at room temperature. Reactions were stopped with 100 ul/well of 3N $H_2SO_4$ and the optical density at 490 nm determined by an automated ELISA reader. Proteins produced by pENV-1, pENV-2, pENV-3, and pENV-5 were all found to be reactive with known seropositive sera.

Further screening of the pENV-1, pENV-3, and pENV-5 encoded protein was carried out using material from the guanidinium chloride-solubilized pellets described above (the pENV-1 encoded protein was further purified by gel-permeation chromatography as described above) against a panel of thirty-one human serum samples. The panel included eight sera from healthy heterosexuals (defined as negative in a whole virus ELISA), two serum pools from AIDS patients, and twenty-one sera from individuals diagnosed as LAS (lymphadenopathy syndrome). Sera from LAS individuals were confirmed as seropositive in a whole virus ELISA. Twelve were further confirmed by Western blot analysis. The results are shown in Table 1. These results demonstrate that sera from AIDS or LAS patients were more reactive with pENV-1, pENV-3, and pENV-5 encoded protein than were sera from normal individuals. This delineation indicates that the trp-env fusion proteins can be used to screen for the presence of sera reactive with the AIDS causative virus, LAV.

TABLE 1

COMPARISON OF pENV1, pENV3, AND pENV5 WITH A WHOLE VIRUS LYSATE IN AN ELISA ASSAY FOR THE DETECTION OF ANTIBODIES TO LAV

| Serum No. | Diagnosis | Whole Virus Lysate[1] | ELISA pENV1 | pENV3 | pENV5 | Confirmed as Seropositive[2] |
|---|---|---|---|---|---|---|
| 501 | Positive control pool | 1.109 | 1.744 | 0.744 | 1.685 | yes |
| Y-1 CDC | Positive control pool | 2.000 | 1.564 | 0.854 | 1.499 | n.d.[4] |
| 120 | LAS[3] and/or homosexual | 1.540 | 1.650 | 1.086 | 1.371 | yes |
| 121 | LAS and/or homosexual | 1.483 | 2.207 | 1.083 | 1.233 | yes |
| 122 | LAS and/or homosexual | 1.283 | 1.318 | 0.752 | 1.465 | yes |
| 124 | LAS and/or homosexual | 1.189 | 2.068 | 1.158 | 1.316 | yes |
| 125 | LAS and/or homosexual | 1.232 | 2.233 | 1.255 | 1.802 | yes |
| 126 | LAS and/or homosexual | 1.233 | 0.878 | 0.689 | 0.816 | yes |
| 127 | LAS and/or homosexual | 1.046 | 1.398 | 0.899 | 1.495 | yes |
| 128 | LAS and/or homosexual | 1.284 | 1.542 | 0.746 | 1.189 | yes |
| 129 | LAS and/or homosexual | 1.081 | 0.719 | 0.484 | 0.944 | yes |
| 130 | LAS and/or homosexual | 0.912 | 1.541 | 1.000 | 1.547 | yes |
| 131 | LAS and/or homosexual | 1.220 | 1.208 | 0.794 | 1.120 | yes |
| 132 | LAS and/or homosexual | 1.237 | 1.245 | 0.735 | 1.127 | yes |
| 133 | LAS and/or homosexual | 1.250 | 1.513 | 0.881 | 1.472 | yes |
| 134 | LAS and/or homosexual | 1.050 | 1.684 | 0.800 | 1.660 | yes |
| 135 | LAS and/or homosexual | 1.310 | 0.705 | 0.516 | 1.005 | yes |
| 138 | LAS and/or homosexual | 1.302 | 0.710 | 0.730 | 0.934 | yes. |
| 153 | LAS and/or homosexual | 2.000 | 1.444 | 0.830 | 1.369 | yes |
| 154 | LAS and/or homosexual | 1.41 | 0.815 | 0.662 | 0.959 | yes |
| 155 | LAS and/or homosexual | 1.069 | 1.824 | 1.199 | 1.644 | yes |
| 157 | LAS and/or homosexual | 1.349 | 1.679 | 1.098 | 1.433 | yes |
| 666 | Unknown | 2.000 | 1.737 | 1.172 | 1.682 | yes |
| 633 | Healthy | 0.222 | 0.089 | 0.113 | 0.135 | not sero- |

TABLE 1-continued

COMPARISON OF pENV1, pENV3, AND pENV5 WITH A WHOLE VIRUS LYSATE IN AN ELISA ASSAY FOR THE DETECTION OF ANTIBODIES TO LAV

| Serum No. | Diagnosis | Whole Virus Lysate[1] | ELISA pENV1 | ELISA pENV3 | ELISA pENV5 | Confirmed as Seropositive[2] |
|---|---|---|---|---|---|---|
| | heterosexual | | | | | positive |
| 637 | Healthy heterosexual | 0.097 | 0.067 | 0.065 | 0.183 | not seropositive |
| 639 | Healthy heterosexual | 0.123 | 0.073 | 0.045 | 0.186 | not seropositive |
| 641 | Healthy heterosexual | 0.199 | 0.100 | 0.075 | 0.236 | not seropositive |
| 667 | Healthy hetersexual | 0.095 | 0.208 | 0.113 | 0.450 | n.d. |
| 1890 | Healthy heterosexual | n.d. | 0.093 | 0.082 | 0.311 | n.d. |
| 1891 | Healthy heterosexual | n.d. | 0.164 | 0.086 | 0.411 | n.d. |
| 1892 | Healthy heterosexual | n.d. | 0.055 | 0.045 | 0.169 | n.d. |
| 1186Z | | | | | | |

[1] Prepared as described in copending patent application U.S.S.N. 558,109, filed December 5, 1983.
[2] Radiolabelled LAV antigens were disrupted in RIPA buffer (Gilead et al., Nature 264:263 (1976)) and then were reacted with human serum. The resultant immune complexes were separated by binding to a *Staphlococcus aureus* adsorbent (Kessler, J. Immunology 115:1617 (1975)) followed by multiple washings. Immune-precipitated antigens were analyzed by SDS Polyacrylamide gel electrophoresis (Laemmli, Nature 227:680 (1970)) followed by fluorography. Presence of either a p25 or gp43 band was considered necessary and sufficient to confirm a sample as seropositive.
[3] LAS = lymphadenopathy syndrome.
[4] n.d. = not done.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A DNA sequence coding for a protein which is immunologically reactive with antibodies to LAV, said sequence corresponding to pENV-1.

2. A DNA sequence coding for a protein which is immunologically reactive with antibodies to LAV, said sequence corresponding to pENV-2.

3. A DNA sequence coding for a protein which is immunologically reactive with antibodies to LAV, said sequence corresponding to pENV-3.

4. A DNA sequence coding for a protein which is immunologically reactive with antibodies to LAV, said sequence corresponding to pENV-4.

5. A DNA sequence coding for a protein which is immunologically reactive with antibodies to LAV, said sequence corresponding to pENV-5.

6. A recombinant plasmid capable of replication in bacterial host cells, said plasmid including procaryotic transcriptional and translational signals for expression, followed in reading phase by a DNA sequence comprising a portion of the env region of the LAV genome, said portion coding for a protein which is immunologically reactive with antibodies to LAV and said portion corresponding to a DNA sequence selected from the group consisting pENV-1, pENV-2, pENV-3, pENV-4 and pENV-5.

7. The recombinant plasmid of claim 6 wherein said expression is inducible.

8. The recombinant plasmid of claim 7 wherein said signals are derived from the trp operon.

9. A bacterial cell stably transformed with a recombinant plasmid capable of replication in bacterial host cells, said plasmid including procaryotic transcriptional and translational signals for expression, followed in reading phase by a DNA sequence comprising a portion of the env region of the LAV genome, said portion coding for a protein which is immunologically reactive with antibodies to LAV and said portion corresponding to a DNA sequence selected from the group consisting of pENV-1, pENV-2, pENV-3, pENV-4, and pENV-5.

10. The transformed cell of claim 9 wherein said bacterial cell is *E. coli*.

11. The transformed cell of claim 9 wherein said expression is inducible.

12. The transformed cell of claim 11 wherein said signals are derived from the trp operon.

13. A method for preparing proteins which are immunologically reactive with antibodies to LAV, comprising:
   introducing into a bacterial host cell a recombinant plasmid capable of replication in bacterial host cells, said plasmid including procaryotic transcriptional and translational signals for expression, followed in reading phase by a DNA sequence comprising a portion of the env region of the LAV genome, said portion coding for a protein which is immunologically reactive with antibodies to LAV and said portion corresponding to a DNA sequence selected from the group consisting of pENV-1, pENV-2, pENV-3, pENV-4 and pENV-5;
   incubating said bacterial host in an appropriate culture medium allowing expression of said protein; and
   isolating the protein product of said sequence from said bacterial host.

14. The method of claim 13, including, after isolation of said protein product, purifying said product of gel permeation chromatography.

15. The method of claim 13 wherein the expression of said protein is induced by 3-β-indoleacrylic acid.

16. The method of claim 13 wherein said expression is inducible.

17. The method of claim 16 wherein said signals are derived from the trp operon.

* * * * *

UNITED STATES PATENT AND TRADEMARK OFFICE
CERTIFICATE OF CORRECTION

PATENT NO. : 5,328,835
DATED : July 12, 1994
INVENTOR(S) : Susan M. Watanabe, Wesley L. Cosand, Susan McArdle and Bruce M. Travis It is certified that error appears in the above-identified patent and that said Letters Patent is hereby corrected as shown below:

On title page, item [75], the Inventors, kindly delete "Suan" and insert --Susan--.

Col. 2, line 46, kindly delete "Sequence" and insert --sequence--.

Col. 3, line 54, kindly delete "HTLV-1II" and insert --HTLV-III--.

Col. 3, line 60, kindly delete "hornology" and insert --homology--.

Col. 5, line 31, kindly delete "a HuIg" and insert --α HuIg--.

Col. 5, line 42, kindly delete "vital" and insert --viral--.

Col. 5, line 55, kindly delete "LAY" and insert --LAV--.

Col. 5, line 56, kindly delete "vital" and insert --viral--.

Col. 6, line 34, kindly delete "i n" and insert --in--.

Col. 6, line 61, kindly delete "MGSO$_4$/50" and insert --MgSO$_4$/50--.

UNITED STATES PATENT AND TRADEMARK OFFICE
CERTIFICATE OF CORRECTION

PATENT NO.  : 5,328,835
DATED       : July 12, 1994
INVENTOR(S) : Susan M. Watanabe, et al It is certified that error appears in the above-indentified patent and that said Letters Patent is hereby corrected as shown below:

Col. 8, line 45, kindly delete "Barn" and insert --Bam--.

Col. 11, line 14, kindly delete "NAC1" and insert --NaCl--.

Signed and Sealed this

Sixth Day of December, 1994

Attest:

BRUCE LEHMAN

Attesting Officer

Commissioner of Patents and Trademarks